United States Patent [19]

Burton et al.

[11] Patent Number: 5,078,720
[45] Date of Patent: Jan. 7, 1992

[54] STENT PLACEMENT INSTRUMENT AND METHOD

[75] Inventors: John H. Burton, Minnetonka; Michael A. Mikulich, Shakopee, both of Minn.

[73] Assignee: American Medical Systems, Inc., Minnetonka, Minn.

[21] Appl. No.: 518,064

[22] Filed: May 2, 1990

[51] Int. Cl.[5] ............................................. A61M 29/00
[52] U.S. Cl. ................................... 606/108; 606/198
[58] Field of Search ............... 606/108, 198, 191, 151

[56] References Cited

U.S. PATENT DOCUMENTS

| | | |
|---|---|---|
| 4,655,771 | 4/1987 | Wallsten . |
| 4,660,560 | 4/1987 | Klein ................................. 606/108 |
| 4,732,152 | 3/1988 | Wallstein et al. . |
| 4,762,128 | 8/1988 | Rosenbluth ....................... 604/96 X |
| 4,768,507 | 9/1988 | Fischell et al. . |
| 4,787,899 | 11/1988 | Lazarus ........................... 606/108 X |

*Primary Examiner*—Michael H. Thaler
*Attorney, Agent, or Firm*—Peter C. Richardson; Lawrence C. Akers; Mark Dryer

[57] ABSTRACT

An instrument for the placement of a self-expanding stent in a body canal, which comprises an elongated inner tube having an outer tube disposed along its axis adapted to carry and retain a self-expanding stent adjacent its proximal end, and an arrangement for releasing the stent, in combination with at least one of the following components: (a) a location member for positioning and fixing the instrument so that the stent is released at a desired location in the body canal, and (b) a member for releasing the stent in a retrograde manner. A method for placing a self-expanding stent in a body canal is also disclosed.

5 Claims, 2 Drawing Sheets

1

STENT PLACEMENT INSTRUMENT AND METHOD

BACKGROUND OF THE INVENTION

This invention relates to an instrument for the placement of a stent in a body canal and particularly to an instrument including means for the correct positioning of a self-expanding stent in a body canal, and means for releasing the stent in a retrograde manner.

Tubular prostheses for transluminal implantation in body canals, for example blood vessels, for the purpose of repair or dilation are known in the art. These prostheses, referred to herein as stents, may be tubular elements which are non-extendible or extendible (i.e. adapted to extend longitudinally), or they may be self-expanding in the transverse direction.

A typical self-expanding stent is disclosed in U.S. Pat. No. 4,655,771, which stent has a radially and axially flexible, elastic tubular body with a predetermined diameter that is variable under axial movement of ends of the body relative to each other and which is composed of a plurality of individually rigid but flexible and elastic thread elements defining a radially self-expanding helix. The disclosure in U.S. Pat. No. 4,655,771 is incorporated herein by reference.

Placement of the stent according to U.S. Pat. No. 4,655,771 in a body vessel is achieved in one embodiment by a device which comprises the use of a piston or, in another embodiment, by use of latch means to push the stent forward.

U.S. Pat. No. 4,768,507 discloses a stent insertion apparatus which includes an inner core member with a spiral groove formed on its outer surface, which groove cooperates with an outer sheathing to form a spiral cavity adapted to contain an expandable coil stent.

U.S. Pat. No. 4,732,152 discloses a device for the implantation of a radially expandable prosthesis comprising hose means for maintaining the prosthesis in a radially contracted state around a concentric flexible probe and means for releasing the prosthesis from said probe.

U.S. patent application Ser. No. 569,267 (now U.S. Pat. No. 5,026,377) describes and claims in combination, a self-expanding braided stent (such as that disclosed in U.S. Pat. No. 4,655,771) and an instrument for the deployment or retraction in a body canal of said stent, which comprises an elongated tubular outer sleeve having a proximal end and a distal end, an elongated core disposed within said sleeve and movable relative to said sleeve, said core being longer than said sleeve and having a proximal end and a distal end and including a grip member at or near said distal end of the core, said grip member being an integral portion of the core or a sleeve or coating attached around the periphery of the core and being adapted to: (i) releasably hold said self-expanding stent within said outer sleeve, (ii) deploy said stent beyond the distal end of said outer sleeve when said outer sleeve is moved in a backward direction relative to said core and (iii) retract said stent back within said outer sleeve when said core is pulled in a backward direction relative to said outer sleeve.

It has now been found that location means for the correct positioning and fixing of the instrument before release of the stent may be incorporated in the instrument. Also means for releasing the stent in a retrograde manner may be incorporated in the instrument. Additionally both said location means and said retrograde releasing means may be combined in a single instrument.

SUMMARY OF THE INVENTION

In accordance with the present invention there is provided an instrument for the placement of a self-expanding stent in a body canal which comprises, an elongated inner tube having a proximal end, a distal end and a central axis, a hollow outer tube disposed about said inner tube along the axis thereof and adapted to carry a self-expanding stent adjacent said proximal end, and means for retaining and releasing said stent, in combination with at least one of the following components:- (a) location means for positioning and fixing the instrument so that the stent is released at a desired location in the body canal; and (b) means for releasing the stent in a retrograde manner.

The invention also provides a method for placing a self-expanding stent at a desired location in a body canal which comprises retaining said stent in an instrument comprising an elongated inner tube having a proximal end, a distal end and a central axis, a hollow outer tube disposed about said inner tube along the axis thereof and adapted to carry said stent adjacent said proximal end, means for retaining and releasing said stent and location means for positioning and fixing the instrument so that the stent is released at said desired location, which method comprises inserting the proximal end of said inner tube in the body canal, moving the tube along the body canal, using the location means to locate the stent at the desired location, operating the releasing means to release the stent at said desired location and withdrawing the instrument from the body canal.

It is to be understood that, as used herein, the term "proximal" means the end or part furthest from the operator of the instrument and the term "distal" means the end or part nearest to the operator. Thus the front end of the instrument which enters the body canal is the proximal end. Also as used herein the term "in a retrograde manner" means that the release operation takes place after the placement of the stent, which manner of operation is "retrograde" in the sense that it is contrary to the normal order (Webster's Seventh new Collegiate Dictionary). Thus, in the preferred embodiment described herein, the stent is placed in the desired location in a body canal, a sleeve which envelops and restrains the stent is moved forward relative to the placement location and the stent located thereat, thus allowing the stent to expand at said location, and the instrument which includes said sleeve is then withdrawn backwardly (a retrograde motion) through the expanded stent.

BRIEF DESCRIPTION OF THE DRAWINGS

A preferred embodiment of the invention is illustrated in the accompanying drawings, in which.

DETAILED DESCRIPTION OF THE INVENTION

Figure 1:
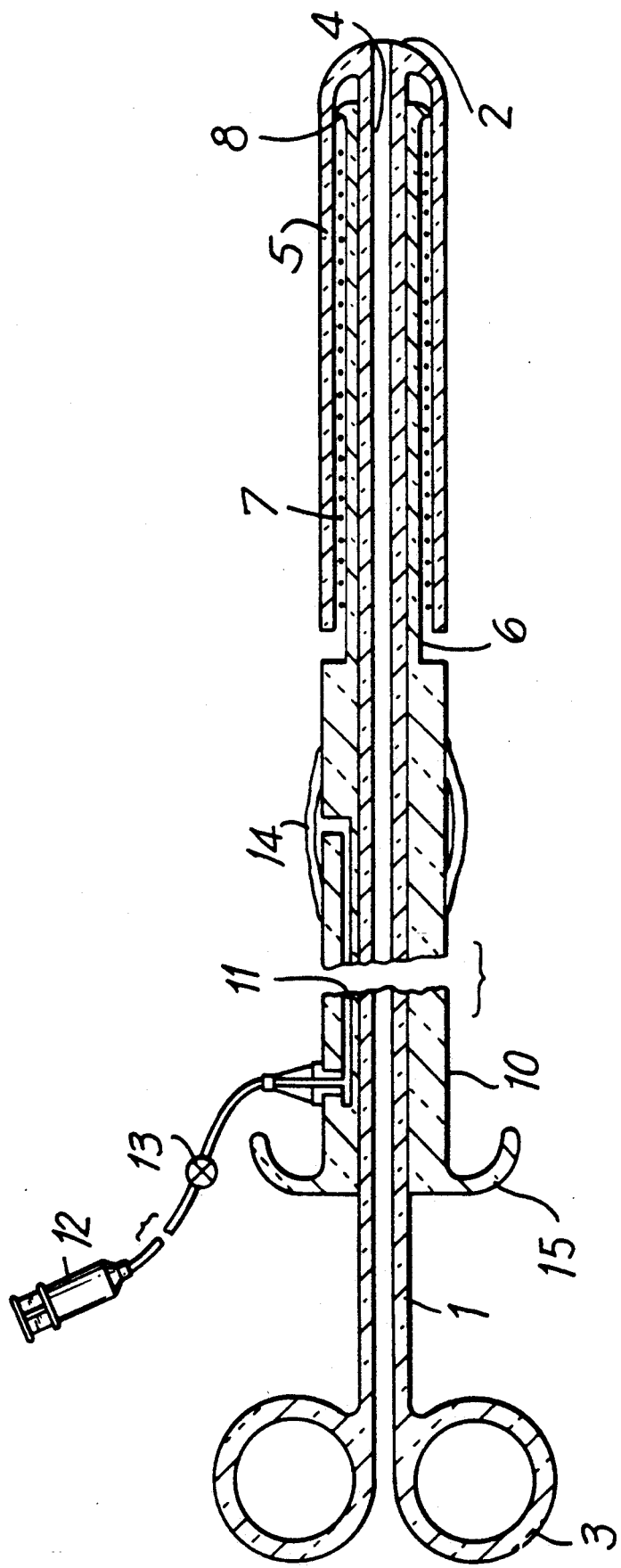
FIG. 1 is a side elevation, partially in section, of an instrument according to the invention.

The type of stent to be placed in a body canal by an instrument according to the invention is preferably a self-expanding stent such as that disclosed and illustrated in U.S. Pat. No. 4,655,771 and the invention will be particularly described hereinafter with reference to such a stent. However, it is to be understood that the instrument according to the invention may be used for the placement of any expansible stent having a configuration and dimensions which enable it to be positioned and released by an instrument according to the invention.

In a preferred embodiment of the invention the inner tube is hollow and this feature may assist in the proper positioning of the instrument in a body canal. Thus it is possible to pass a guide wire into and along the body canal and pass the instrument over the guide wire until it is properly positioned in the body canal, for example, with the aid of the location means described hereinafter.

Thus, the instrument may be used in conjunction with an elongated, flexible steerable guide wire located within and along the axis of the inner tube. When the instrument is positioned in the body canal the guide wire may be retained within the instrument until the stent is released at the desired location and withdrawn together with the instrument or, alternatively the guide wire may be withdrawn prior to release of the stent so that correct positioning of the stent, while still within the instrument, may be verified, for example, by endoscopic or fluoroscopic means.

In a preferred embodiment of the invention the location means comprises a radially expandable stop adapted to be expanded at a predetermined location in said body canal. Alternatively, the location means may be a nodule or flange attached to the instrument at an appropriate position where it may be used to locate the instrument by palpation.

A particularly preferred embodiment of the invention is an instrument for the placement of a self-expanding stent in the prostatic urethra, in which the location means is a radially expandable stop which comprises an inflatable balloon which is adapted, when inflated, to be positioned adjacent the external sphincter at a predetermined distance from the prostate so that the stent will be released at the desired location within the prostatic urethra. The invention will be more particularly described hereinafter with reference to this preferred embodiment.

The preferred means for retaining the stent and for releasing the stent in a retrograde manner comprises an outer sleeve which envelopes and restrains the stent, which sleeve is integral with the proximal end of the inner tube and extends distally around the outer tube carrying the stent, and is adapted to be pushed proximally relative to the stent so that the stent is then no longer restrained and is allowed to expand and be released at the desired location in the body canal, said outer sleeve being further adapted to be withdrawn when said instrument is removed from the body canal.

In performing the method of the invention as described above the stent is released from the instrument in a retrograde manner for which purpose the means for releasing the stent comprises an outer sleeve which envelopes and restrains the stent, and the stent is released at the desired location by pushing said sleeve proximally relative to the stent so that the stent is no longer restrained and is allowed to expand and be released at the desired location.

The instrument illustrated in FIG. 1 of the drawings comprises an elongated hollow inner tube 1 having a proximal end 2 and a distal end 3. In the embodiment shown in FIG. 1 the distal end of the tube terminates in ring handles but these are not shown in FIG. 2. The tube comprises an elongated hollow inner tube 4 which extends the full length of the instrument and which is turned back on itself at the proximal end to form an integral outer sleeve 5.

A hollow outer tube 6 disposed about the inner tube along the axis thereof and slidably positioned around the inner tube 4 carries a self-expanding stent 7. The stent is represented schematically by a series of dots in FIG. 1 and is shown partially expanded in FIG. 2. Preferably, the proximal end of the outer tube 6 terminates in an annular flange 8 to prevent the stent from prematurely sliding off the end of the tube. Before placement, the stent is retained within the instrument by the outer sleeve 5 and, in the condition shown in FIG. 2, the stent is partially released in the prostatic urethra 9. The distal portion 10 of the hollow outer tube is somewhat thicker than the proximal portion and contains a lumen 11 through which may be pumped fluid from a syringe 12, controlled by a valve 13, to dilate a location balloon 14.

In the embodiment illustrated in FIG. 1 the distal end of the outer tube terminates in a curved handle 15. Alternatively the handle may be a ring handle similar to that shown at the distal end of the elongated inner tube. The handle is not shown in FIG. 2.

Figure 2:
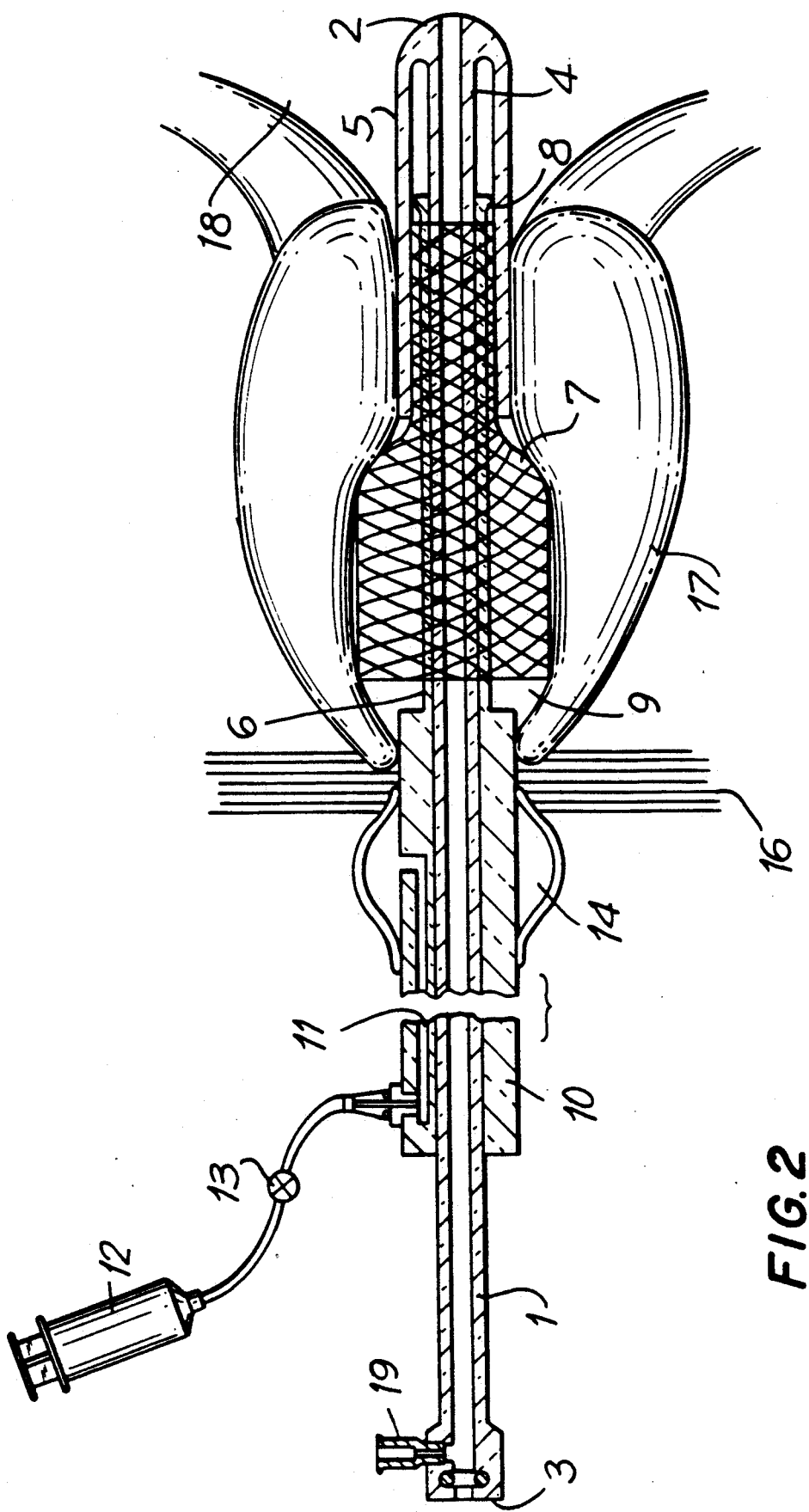
FIG. 2 illustrates an instrument, similar to that shown in FIG. 1, positioned within a urethra.

When the location balloon is positioned against the external sphincter 16 as shown in FIG. 2 it is inflated to position and fix the instrument at the desired location. If desired, the location balloon may be partially inflated when the instrument is introduced in the urethra to facilitate correct positioning, for example, by palpation. Thus, when the location balloon is correctly positioned, the stent will be properly located against the prostate 17 and the stent may then be released from the instrument by retrograde movement of the outer sleeve 5. This movement is achieved by holding the handle 15 (FIG. 1) and pushing the hollow inner tube 4 from the distal end 3 so that the proximal end 2 extends into the bladder 18. The retrograde movement is continued until the distal end of the outer sleeve is clear of the proximal end of the stent, whereupon the stent expands, is released from the instrument and presses against the prostate.

In the embodiment illustrated in FIG. 2 the outer tube 6 is made of a transparent plastics material so that correct placement of the stent 7 may be facilitated by endoscopic means, indicated schematically by the eyepiece 19, as well as by the location balloon 14. Also, in this embodiment the elongated hollow inner tube 1 is preferably a substantially rigid transparent tube.

We claim:

1. An instrument for the placement of a self-expanding stent in the prostatic urethra which comprises, a substantially rigid elongated inner tube having a proximal end, a distal end and a central axis, a hollow outer tube disposed about said inner tube along the axis thereof and adapted to carry a self-expanding stent adjacent said proximal end, and means for retaining and releasing said stent, in combination with at least one of the following components:- (a) location means for positioning and fixing the instrument so that the stent is released at a desired location within the prostatic urethra, which location means comprises an inflatable balloon which is adapted, when inflated, to be positioned adjacent the external sphincter at a predetermined distance from the prostate so that the stent will be released at the desired location within the prostatic urethra, and (b) means for releasing the stent in a retrograde manner.

2. A combination according to claim 1, in which the means for retaining the stent and for releasing the stent in a retrograde manner comprises an outer sleeve which envelopes and restrains the stent, which sleeve is integral with the proximal end of the inner tube and extends distally around the outer tube carrying the stent, and is adapted to be pushed proximally relative to the stent so that the stent is then no longer restrained and is allowed to expand and be released at the desired location in the body canal, said outer sleeve being further adapted to be withdrawn when said instrument is removed from the body canal.

3. A combination according to claim 1, in which proximal end of the hollow outer tube terminates in an annular flange.

4. A method for placing a self-expanding stent at a desired location in the prostatic urethra which comprises retaining said stent in an instrument comprising a substantially rigid elongated inner tube having a proximal end, a distal end and a central axis, a hollow outer tube disposed about said inner tube along the axis thereof and adapted to carry said stent adjacent said proximal end, means for retaining and releasing said stent and location means for positioning and fixing the instrument so that the stent is released at said desired location, which location means comprises an inflatable balloon which is adapted, when inflated, to be positioned adjacent the external sphincter at a predetermined distance from the prostate so that the stent will be released at the desired located within the prostatic urethra, which method comprises inserting the proximal end of said tube in the urethra, moving the instrument along the urethra, using the location means to locate the stent at the desired location, operating the releasing means to release the stent at said desired location and withdrawing the instrument from the urethra.

5. A method according to claim 4, in which said means for releasing the stent is adapted to release the stent in a retrograde manner and comprises an outer sleeve which is integral with the proximal end of the inner tube and extends distally around the outer tube carrying the stent whereby it envelopes and restrains the stent, and the stent is released at the desired location by pushing said sleeve proximally relative to the stent so that the stent is no longer restrained and is allowed to expand and be released at said desired location.

* * * * *